(12) United States Patent
Jiang et al.

(10) Patent No.: US 12,274,582 B2
(45) Date of Patent: Apr. 15, 2025

(54) ULTRASOUND ELASTOGRAPHY METHOD AND SYSTEM

(71) Applicant: SHENZHEN MINDRAY BIO-MEDICAL ELECTRONICS CO., LTD., Guangdong (CN)

(72) Inventors: Peng Jiang, Shenzhen (CN); Shuangshuang Li, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 220 days.

(21) Appl. No.: 17/067,436

(22) Filed: Oct. 9, 2020

(65) Prior Publication Data

US 2021/0022711 A1    Jan. 28, 2021

Related U.S. Application Data

(63) Continuation of application No. PCT/CN2018/082691, filed on Apr. 11, 2018.

(51) Int. Cl.
    *A61B 8/08*      (2006.01)
    *A61B 8/00*      (2006.01)
    *A61B 8/14*      (2006.01)

(52) U.S. Cl.
    CPC .............. *A61B 8/485* (2013.01); *A61B 8/145* (2013.01); *A61B 8/4444* (2013.01);
(Continued)

(58) Field of Classification Search
CPC ....... A61B 8/485; A61B 8/145; A61B 8/4444; A61B 8/4494; A61B 8/5223; A61B 8/54
See application file for complete search history.

(56) References Cited

U.S. PATENT DOCUMENTS 11,172,910 B2    11/2021    Greenleaf et al.
2008/0249408 A1*   10/2008    Palmeri ................ A61B 8/08
                                                  600/438
(Continued)

FOREIGN PATENT DOCUMENTS

CN         102283679 A      12/2011
CN         102667522 A1     9/2012
(Continued)

OTHER PUBLICATIONS

Chen S, Urban MW, Pislaru C, Kinnick R, Zheng Y, Yao A, Greenleaf JF. Shearwave dispersion ultrasound vibrometry (SDUV) for measuring tissue elasticity and viscosity. IEEE Trans Ultrason Ferroelectr Freq Control. Jan. 2009;56(1):55-62. doi: 10.1109/TUFFC.2009.1005. PMID: 19213632; PMCID: PMC2658640. (Year: 2009).*

(Continued)

*Primary Examiner* — Yi-Shan Yang
*Assistant Examiner* — Nicholas A Robinson
(74) *Attorney, Agent, or Firm* — Sheppard Mullin Richter & Hampton LLP

(57) ABSTRACT

An ultrasound elastography method and system are provided. The method may include: exciting an ultrasound probe to transmit ultrasound waves to a body tissue under examination and receive ultrasound echoes to obtain a first ultrasound echo signal, wherein the ultrasound probe comprises an ultrasound transducer provided with multiple array elements; obtaining an ultrasound image of a body tissue under examination; displaying the ultrasound image; generating a shear waves within the body tissue under examination; exciting array elements of a ultrasound transducer to transmit the ultrasound waves to form an ultrasound beam covering a first region within the body tissue under examination; receiving the ultrasound echoes from the first region
(Continued)

to obtain the second ultrasound echo signal; and obtaining the propagation path of the shear waves within the first region according to the second ultrasound echo signal.

15 Claims, 5 Drawing Sheets

(52) U.S. Cl.
CPC ............ *A61B 8/4494* (2013.01); *A61B 8/463* (2013.01); *A61B 8/5223* (2013.01); *A61B 8/54* (2013.01); *A61B 8/4488* (2013.01)

(56) References Cited

U.S. PATENT DOCUMENTS

| | | | |
|---|---|---|---|
| 2009/0216119 | A1 | 8/2009 | Fan et al. |
| 2010/0016718 | A1 | 1/2010 | Fan et al. |
| 2011/0263978 | A1* | 10/2011 | Chen ................. A61B 8/485 600/438 |
| 2013/0131511 | A1 | 5/2013 | Peterson et al. |
| 2013/0218012 | A1* | 8/2013 | Specht ............... G01S 15/8929 367/7 |
| 2013/0317361 | A1 | 11/2013 | Tabaru et al. |
| 2016/0143621 | A1 | 5/2016 | Parthasarathy et al. |
| 2016/0262706 | A1* | 9/2016 | Zhao ..................... A61B 5/055 |
| 2019/0046160 | A1 | 2/2019 | Li et al. |
| 2019/0192120 | A1* | 6/2019 | Choi ..................... A61B 8/54 |
| 2019/0314002 | A1 | 10/2019 | Peterson et al. |
| 2020/0187910 | A1* | 6/2020 | Pinton .................. A61B 8/085 |

FOREIGN PATENT DOCUMENTS

| | | |
|---|---|---|
| CN | 103347450 A | 10/2013 |
| CN | 103492855 A | 1/2014 |
| CN | 105395218 A | 3/2016 |
| CN | 105491959 A | 4/2016 |
| CN | 105877783 A | 8/2016 |
| CN | 205697832 U | 11/2016 |
| CN | 106456108 A | 2/2017 |
| CN | 107510474 A | 12/2017 |
| JP | 2015-188514 A | 11/2015 |
| WO | 2016/033752 A1 | 3/2016 |

OTHER PUBLICATIONS

PCT International Search Report and the Written Opinion mailed Jan. 14, 2019, issued in related International Application No. PCT/CN2018/082691, with partial English translation (11 pages).
PCT International Preliminary Report on Patentability mailed Oct. 22, 2020, issued in related International Application No. PCT/CN2018/082691, with English translation (10 pages).
First Search dated Oct. 18, 2021, issued in related Chinese Application No. 201880016644.6 (2 pages).
First Office Action dated Oct. 26, 2021, issued in related Chinese Application No. 201880016644.6, with English machine translation (23 pages).

* cited by examiner

ULTRASOUND ELASTOGRAPHY METHOD AND SYSTEM

CROSS-REFERENCE TO RELATED APPLICATION

This application is a continuation application of International Patent Application No. PCT/CN2018/082691, filed with the China National Intellectual Property Administration (CNIPA) of People's Republic of China on Apr. 11, 2018, and entitled "ULTRASOUND ELASTOGRAPHY METHOD AND SYSTEM". The entire content of the above-identified application is incorporated herein by reference.

TECHNICAL FIELD

The present disclosure relates to ultrasound imaging, in particular to an ultrasound elastography method and system.

BACKGROUND

Transient elastography is a method for measuring tissue stiffness, which is mainly used in the clinical diagnosis of liver. Many chronic liver diseases will be accompanied by the process of liver fibrosis, during which the elasticity of the liver gradually changes and eventually leads to cirrhosis. The transient elastography can non-invasively monitor the changes in this process and provide a basis for clinical diagnosis.

In the transient elastography, mechanical vibration pulses may be used to excite the tissue to generate transient shear waves in the tissue, and a fast ultrasound imaging system may be used to collect radio frequency data and estimate the tissue displacement, so as to obtain the propagation of the shear waves in the tissue, which may be used to calculate the hardness of the tissue.

The traditional transient elastography systems are all one-dimensional systems, and can only obtain the average elastic results of a small region of the body tissue in one direction at the center of the probe during the measurement. The diagnosis range is small, and the image of the internal of the body tissue under examination cannot be provided to the doctor. Therefore, the doctor cannot observe the internal of the body tissue under examination during the transient elasticity measurement, and can only adjust the position of the probe by experience to aim the probe to the tissue desired to be measured, which is inconvenient.

SUMMARY

In one embodiment, an ultrasound elastography method is provided, which may include: exciting an ultrasound probe to transmit ultrasound waves to a body tissue under examination and receive ultrasound echoes to obtain a first ultrasound echo signal, where the ultrasound probe comprises an ultrasound transducer provided with multiple array elements; obtaining an ultrasound image of the body tissue under examination according to the first ultrasound echo signal; displaying the ultrasound image; generating a shear waves in the body tissue under examination; exciting at least part of the array elements of the ultrasound transducer to transmit ultrasound waves and control an excitation time of each array element to be excited such that the ultrasound waves transmitted by the excited array elements form an ultrasound beam covering a first region in the body tissue under examination, wherein the shear wave propagates at least partially in the first region; receiving ultrasound echoes from the first region to obtain a second ultrasound echo signal; and obtaining a propagation path of the shear wave in the first region according to the second ultrasound echo signal.

In one embodiment, an ultrasound elastography system is provided, which may include: an ultrasound probe including a vibrator and an ultrasound transducer provided with multiple array elements, where the vibrator is able to drive the ultrasound transducer to vibrate to generate a shear wave in a body tissue under examination; a control and data processor which is configured to control the ultrasound transducer and the vibrator and process data obtained by the ultrasound transducer; and a display device which is configured to display data output by the control and data processor. The control and data processor is further configured to: excite the ultrasound transducer to transmit ultrasound waves to the body tissue under examination and receive ultrasound echoes to obtain a first ultrasound echo signal; obtain an ultrasound image of the body tissue under examination according to the first ultrasound echo signal; control the vibrator to drive the ultrasound transducer to vibrate to generate the shear wave in the body tissue under examination; excite at least part of the array elements of the ultrasound transducer to transmit ultrasound waves and control an excitation time of each array element to be excited such that the ultrasound waves transmitted by the excited array elements form an ultrasound beam covering a first region in the body tissue under examination, wherein the shear wave propagates at least partially in the first region; receiving the ultrasound echo from the first region to obtain a second ultrasound echo signal; receive ultrasound echoes from the first region to obtain a second ultrasound echo signal; and control the display device to display the ultrasound image.

In one embodiment, an ultrasound elastography method is provided, which may include: generating a shear wave in a body tissue under examination; exciting at least part of array elements of an ultrasound transducer to transmit ultrasound waves and control an excitation time of each array element to be excited such that the ultrasound waves transmitted by the excited array elements form an ultrasound beam covering a first region in the body tissue under examination, wherein the shear wave propagates at least partially in the first region; receiving ultrasound echoes from the first region to obtain a second ultrasound echo signal; adjusting the excitation time of the array elements to be excited in the ultrasound transducer to change a direction of the ultrasound beam formed by the ultrasound waves transmitted by the excited array element such that the ultrasound beam formed by the ultrasound waves transmitted by the excited array elements covers a second region in the body tissue under examination, wherein the shear wave propagates at least partially in the second region; receiving ultrasound echoes from the second region to obtain a third ultrasound echo signal; and obtaining a propagation path of the shear wave in a two-dimensional region comprising the first region and the second region according to at least the second ultrasound echo signal and the third ultrasound echo signal.

In one embodiment, an ultrasound elastography method is provided, which may include: generating a shear wave in a body tissue under examination; exciting at least part of array elements of an ultrasound transducer to transmit ultrasound waves and control an excitation time of each array element to be excited such that the ultrasound waves transmitted by the excited array elements form an ultrasound beam covering a first region in the body tissue under examination, wherein the shear wave propagates at least partially in the first region; receiving ultrasound echoes from the first region to obtain a second ultrasound echo signal; generating the shear wave in the body tissue under examination again; exciting at least part of array elements of an ultrasound transducer to transmit ultrasound waves and control an excitation time of each array element to be excited such that the ultrasound waves transmitted by the excited array elements form an ultrasound beam covering a second region in the body tissue under examination, wherein the shear wave propagates at least partially in the second region; receiving ultrasound echoes from the second region to obtain a third ultrasound echo signal; and obtaining a propagation path of the shear wave in a two-dimensional region comprising the first region and the second region according to at least the second ultrasound echo signal and the third ultrasound echo signal.

In one embodiment, an ultrasound elastography method is provided, which may include: exciting an ultrasound probe to transmit ultrasound waves to a body tissue under examination and receive ultrasound echoes to obtain a first ultrasound echo signal, wherein the ultrasound probe comprises an ultrasound transducer provided with multiple array elements; obtaining an ultrasound image of the body tissue under examination according to the first ultrasound echo signal; displaying the ultrasound image; determining a region of interest in the ultrasound image; based on the determined region of interest, generating a shear wave in the body tissue under examination such that the generated shear wave at least partially propagates in the region of interest; exciting at least part of the array elements of the ultrasound transducer to transmit ultrasound waves and controlling an excitation time of each array element to be excited such that the ultrasound waves transmitted by the excited array elements form an ultrasound beam covering the region of interest; receiving ultrasound echoes from the region of interest to obtain an ultrasound echo signal; and obtaining a propagation path of the shear wave in the region of interest according to the ultrasound echo signal.

In one embodiment, an ultrasound elastography system is provided, which may include: an ultrasound probe comprising a vibrator and an ultrasound transducer provided with multiple array elements, where the vibrator is able to drive the ultrasound transducer to vibrate to generate a shear wave in a body tissue under examination; a control and data processor which is configured to control the ultrasound transducer and the vibrator and process data obtained by the ultrasound transducer; and a display device which is configured to display data output by the control and data processor. The control and data processor is further configured to: excite the ultrasound probe to transmit ultrasound waves to the body tissue under examination and receive ultrasound echoes to obtain a first ultrasound echo signal; obtain an ultrasound image of the body tissue under examination according to the first ultrasound echo signal; display the ultrasound image; determine a region of interest in the ultrasound image; based on the determined region of interest, control the vibrator to drive the ultrasound transducer to vibrate to generate a shear wave in the body tissue under examination such that the generated shear wave at least partially propagates in the region of interest; excite at least part of the array elements of the ultrasound transducer to transmit ultrasound waves and controlling an excitation time of each array element to be excited such that the ultrasound waves transmitted by the excited array elements form an ultrasound beam covering the region of interest; receive ultrasound echoes from the region of interest to obtain an ultrasound echo signal; and obtain a propagation path of the shear wave in the region of interest according to the ultrasound echo signal.

The details of one or more embodiments of the present disclosure will be described in the following drawings and description. Other features, objects and advantages of the present disclosure will become apparent from the description, drawings and claims.

BRIEF DESCRIPTION OF THE DRAWINGS

In order to describe the embodiments of the present disclosure or the technical solutions in the prior art more clearly, the drawings to be used in the description of the embodiments or the prior art will be briefly described below. Obviously, the drawings described below are only some examples of the present disclosure. For those of ordinary skill in the art, the drawings of other embodiments may be obtained based on these drawings without creative works.

DETAILED DESCRIPTION

Figure 1:
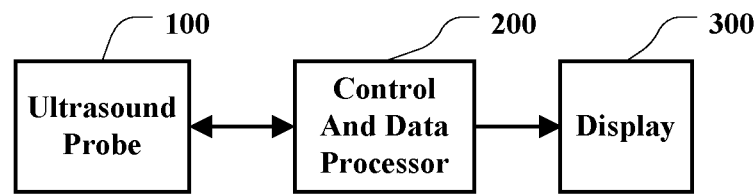
FIG. 1 is a schematic block diagram of a transient elastography system in one embodiment.

In order to facilitate the understanding to the present disclosure, the present disclosure will be described more fully below with reference to the drawings. The embodiments of the present disclosure are shown in the drawings. However, the present disclosure can be implemented in many different ways, but not limited to the embodiments described herein. On the contrary, the purpose of providing these embodiments is to make the present disclosure to be understood more thoroughly and comprehensively.

It should be noted that when an element is described as being "fixed to" another element, it may be directly fixed on the other element or an intermediate element may exist. When an element is described as being "connected" to another element, it can be directly connected to the other element or an intermediate element may exist. The terms "vertical", "horizontal", "left", "right" or similar expressions used herein are for illustrative purposes only, but not mean that it is the only implementation.

Unless otherwise defined, all technical and scientific terms used herein have the same meaning as commonly understood by those skilled in the technical field of the present disclosure. The terms used in the description of the present disclosure are only for the purpose of describing the specific embodiments, but not intended to limit the present disclosure. The term "and/or" as used herein will include any and all combinations of the one or more related listed items.

Referring to FIG. 1, in one embodiment, an ultrasound elastography system may include an ultrasound probe 100, a control and data processor 200 and a display 300.

The control and data processor 200 may control the ultrasound probe 100 to transmit ultrasound waves to a body tissue under examination, and receive the ultrasound echoes carrying tissue information reflected from the body tissue under examination and convert the ultrasound echoes into electrical signals to obtain ultrasound echo signals. The control and data processor 200 may receive these ultrasound echo signals and process the ultrasound echo signals to obtain an ultrasound image of the body tissue under examination. Depending on the desired imaging mode, the processing performed by the control and data processor 200 on the ultrasound echo signals may be different, which will not be described in detail here. The obtained ultrasound image may be displayed on the display 300.

Figure 2:
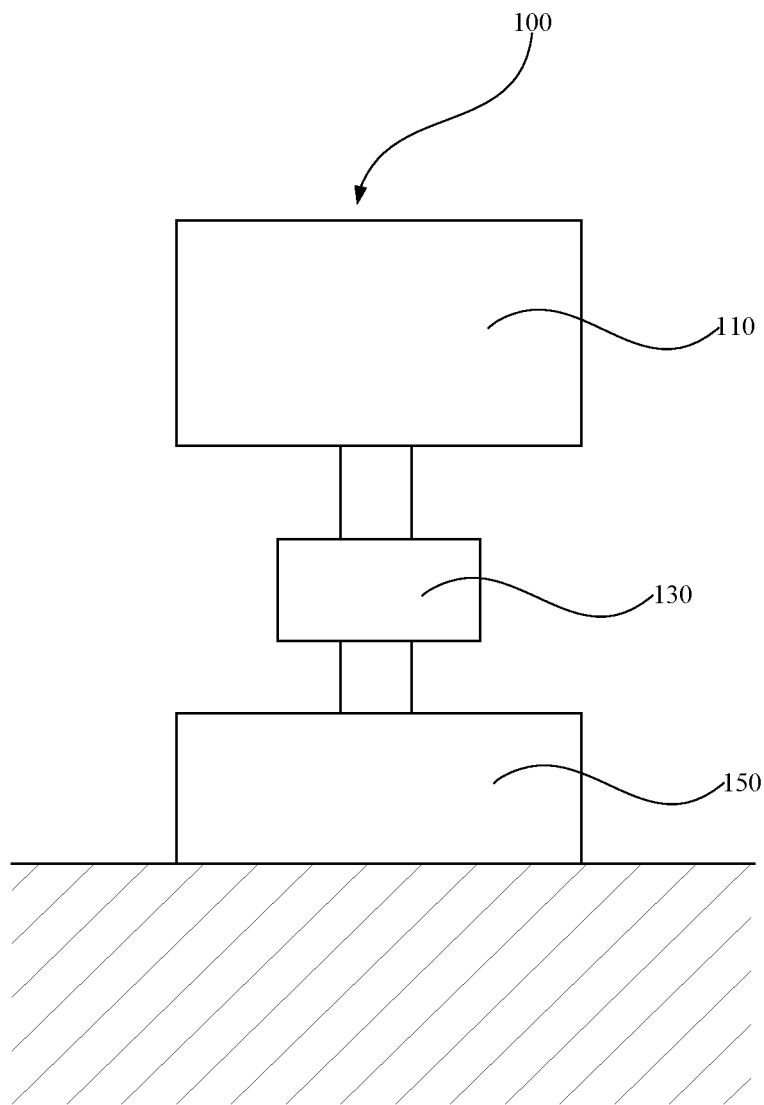
FIG. 2 is a schematic structural diagram of an ultrasound probe in one embodiment.

Referring to FIG. 2, in one embodiment, the ultrasound probe 100 may include a vibrator 110 and an ultrasound transducer 150. The ultrasound transducer 150 may include multiple array elements which may be arranged in a one-dimensional or two-dimensional array. The control and data processor 200 may control the vibrator 110 to vibrate, thereby driving the ultrasound transducer 150 to vibrate. During the operation, the ultrasound probe 100 may be attached to the surface of the tissue under examination. At this time, the vibrator 110 may drive the ultrasound transducer 150 to vibrate, so as to generate a shear wave in the body tissue under examination which propagates from the contact position of the body tissue with the ultrasound transducer 150 to the inside of the body tissue under examination. The control and data processor 200 may control the ultrasound transducer 150 to transmit ultrasound waves to the body tissue under examination to track the shear waves, as described in detail later.

In one embodiment, the ultrasound probe 100 may further include a pressure sensor 130. The pressure sensor 130 may sense the pressure between the ultrasound probe 100 (or the ultrasound transducer 150) and the body tissue under examination, and feed the pressure to the control and data processor 200.

In one embodiment, the shear wave may not be generated by the ultrasound transducer 150 driven by the vibrator 110, but by a separate vibrator (not shown in the figure) provided separately from the ultrasound probe 100, and the multi-element ultrasound transducer 150 of the ultrasound probe 100 may transmit ultrasound waves to track the shear wave. In this embodiment, the vibrator 110 may not be included in the ultrasound probe 100.

Figure 3:
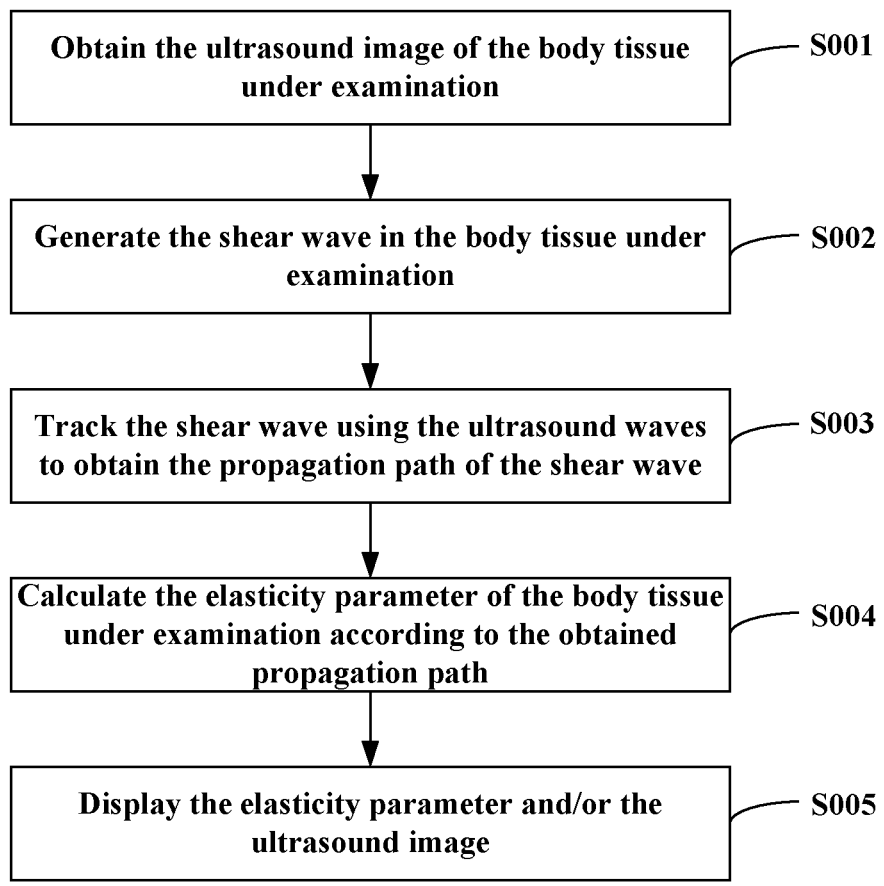
FIG. 3 is a schematic flow chart of an ultrasound elastography method in one embodiment.

Referring to FIG. 3, in one embodiment, an ultrasound elastography method implemented using the ultrasound elastography system above, such as a transient elastography method, may include the following steps.

In step S001, an ultrasound image of the tissue under examination may be obtained.

In this embodiment, when the elasticity parameters or elasticity images of the body tissue under examination are obtained (detailed below), the conventional ultrasound images of the body tissue under examination, such as B-mode images, C-mode images, D-mode images or other ultrasound images, may also be obtained. The obtained conventional ultrasound images may be displayed on the display 300, so that the doctor can observe the condition of the body tissue under examination when scanning the body tissue under examination to obtain the elasticity parameters or elasticity image of the body tissue, thereby facilitating the obtaining of the elasticity of the body tissue under examination.

In this step, the control and data processor 200 may excite the ultrasound transducer 150 of the ultrasound probe 100 to transmit ultrasound waves to the body tissue under examination and receive the ultrasound echoes to obtain the ultrasound echo signals. Herein, the ultrasound echo signals used to obtain the conventional ultrasound images will be referred to as the first ultrasound echo signals. The control and data processor 200 may receive the first ultrasound echo signals and perform corresponding processing on them, thereby obtaining the ultrasound image of the body tissue under examination according to the first ultrasound echo signals, such as B-mode images, C-mode images, D-mode images or other ultrasound images. The obtained ultrasound images may be displayed on the display 300.

In step S002, a shear wave may be generated in the body tissue under examination.

Figure 4:
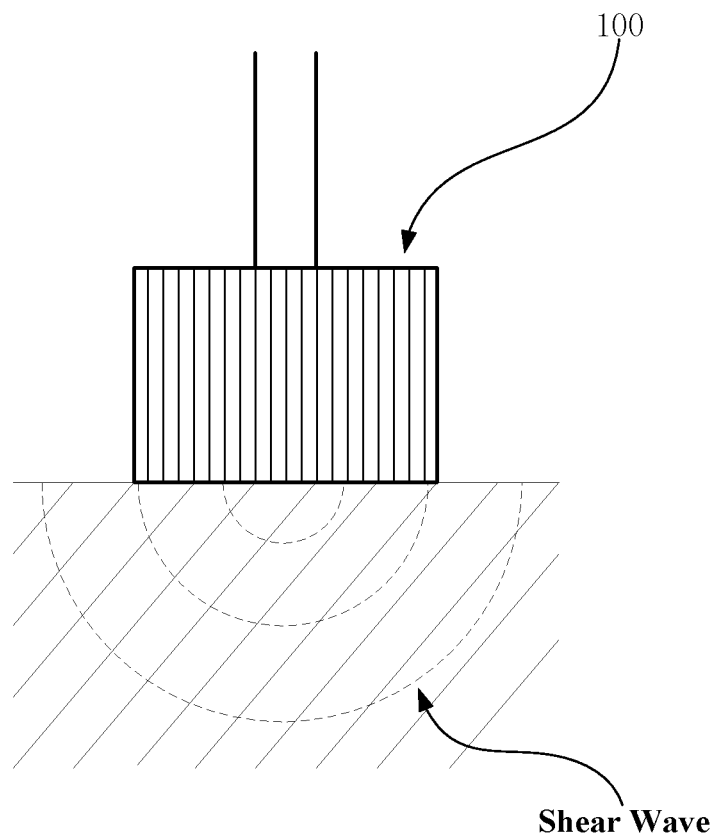
FIG. 4 schematically shows the generation of the shear waves through the ultrasound probe.

In this step, the shear wave may be generated in the body tissue under examination. For example, as described above, the control and data processor 200 may control the vibrator 110 in the ultrasound probe 100 to vibrate to drive the ultrasound transducer 150 that is attached to the surface of the body tissue under examination to vibrate, thereby generate the shear wave propagating inward from the position where the ultrasound transducer 150 is attached to the body tissue under examination. As shown in FIG. 4, in a two-dimensional plane, the shear wave generated in this way is roughly like a corrugation formed by the surface of the water where rocks are thrown into it, which spreads into the tissue under examination from the contact point between the ultrasound probe 100 and the tissue under examination. In this process, the ultrasound transducer 150 may usually be attached to the surface of the body tissue under examination in certain pressure. The pressure may be sensed by the pressure sensor 130 in the ultrasound probe 100 and fed back to the control and data processor 200. The control and data processor 200 may output the current pressure sensed by the pressure sensor 130 to the user in various ways. For example, the current pressure sensed may be output to the user through numbers, graphics, sound or light signals, etc.

In other embodiments, the shear wave may also be generated by a separate vibrator provided separately from the ultrasound probe 100.

In step S003, ultrasound waves may be used to track the shear wave to obtain the propagation path of the shear wave.

After the shear wave is generated in step S002, the control and data processor 200 may send excitation pulses to the ultrasound transducer 150 to excite at least part of the array elements in the ultrasound transducer 150 to transmit the ultrasound waves to the body tissue under examination. Each time the ultrasound waves are transmitted, all or a part of the array elements in the ultrasound transducer 150 may participate in the transmitting. By controlling the time when the array elements participating in the transmitting (i.e., the array elements to be excited in this transmitting) are excited by the excitation pulses, the direction and/or width of the ultrasound beam finally formed by the ultrasound waves transmitted by these array elements participating in this transmitting can be adjusted, such that the ultrasound waves transmitted by the array elements participating in the transmitting form an ultrasound beam that propagates along a desired angle or in a desired region (in other words, covers the desired region). In this embodiment, the control and data processor 200 may control the time when the array elements to be excited (i.e., the array elements participating in the current transmitting) are excited by the excitation pulses, such that the ultrasound waves transmitted thereby form an ultrasound beam covering a first region of the body tissue under examination in which the generated shear wave at least partly propagates. Therefore, this ultrasound beam can track the propagation process of the shear wave in this first region.

In this embodiment, the ultrasound beam formed by the ultrasound waves transmitted by the at least part of the array elements may be a focused ultrasound beam or an unfocused ultrasound beam, such as a plan ultrasound beam or a diverged ultrasound beam.

The ultrasound transducer 150 may receive the ultrasound echoes from the first region to obtain the ultrasound echo signals. Herein, the ultrasound echo signals obtained from the ultrasound echoes from the first region will be referred to as the second ultrasound echo signals.

Figure 5:
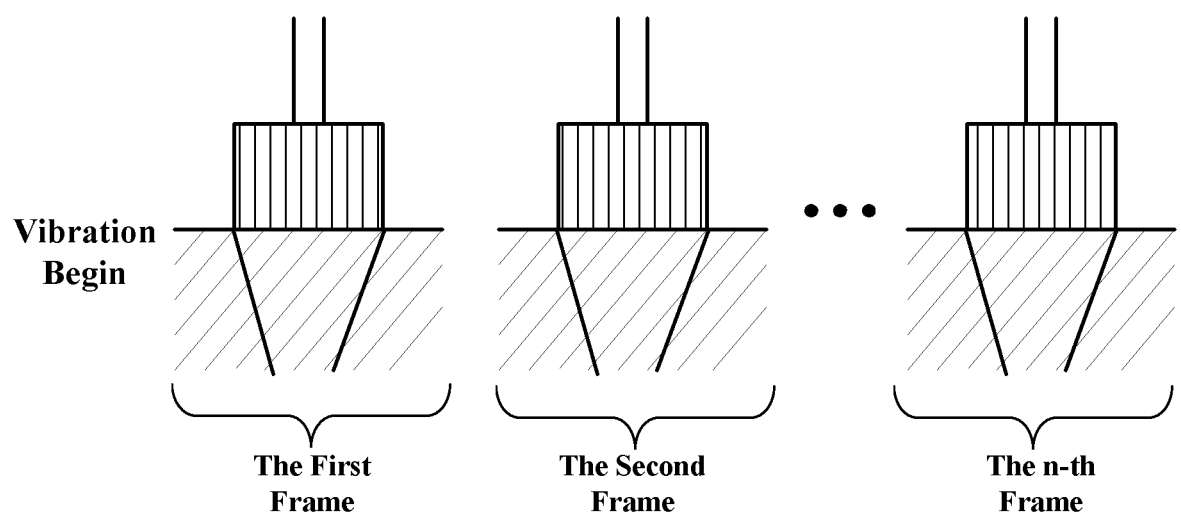
FIG. 5 schematically shows the scanning process in one embodiment.

The process of transmitting the ultrasound beam covering the first region and receiving the ultrasound echoes to obtain the second ultrasound echo signals may be repeated multiple times, as shown in FIG. 5.

The control and data processor 200 may receive the second ultrasound echo signals and process them, so as to obtain the propagation path of the shear wave in the first region. For example, the control and data processor 200 may perform calculations on the second ultrasound echo signals obtained multiple times so as to obtain the propagation path of the shear wave in the first region.

In step S004, the elasticity parameters of the body tissue under examination may be calculated according to the obtained shear wave propagation path.

After obtaining the propagation path of the shear wave in the first region, the control and data processor 200 may calculate the elasticity parameters representing the elasticity of the body tissue under examination in the first region according to the propagation path of the shear wave in the first region. The elasticity parameter may be the propagation speed of the shear wave in the first region, the Young's modulus of the body tissue under examination in the first region, the shear modulus of the body tissue under examination in the first region, the attenuation of the shear wave in the tissue under examination in the first region or the ratio of elasticity parameters of the body tissues under examination at different positions in the first region, etc.

For example, in one embodiment, the displacement of the shear wave within a certain time may be calculated according to the obtained propagation path of the shear wave in the first region, and the propagation speed of the shear wave in the first region may be obtained by the displacement divided by the time. The propagation speed calculated here may be the shear wave propagation speed at various depths in the first region, or may also be the average value of the shear wave propagation speed within any depth range.

In addition, in one embodiment, other elasticity parameters of the body tissue under examination in the first region may be calculated according to the propagation speed of the shear wave in the first region.

For example, the Young's modulus of the tissue may be calculated based on the shear wave propagation speed using the following formula:

$$E = 3\rho V^2$$

Where E is the Young's modulus, representing the hardness of the body tissue under examination; $\rho$ is the tissue density of the tissue under examination; and V is the shear wave propagation speed in the tissue under examination.

Other parameters representing the elasticity of the body tissue under examination in the first region, such as the shear modulus, the attenuation of the shear wave or the like, may also be calculated using corresponding methods, which will not be listed here.

In step S006, the elasticity parameters and/or the ultrasound images of the body tissue under examination may be displayed.

After obtaining the elasticity parameters, the obtained elasticity parameters may be displayed on the display 300. These elasticity parameters may be displayed in numerical values, colors, graphs or the like. In one embodiment, the propagation path of the shear wave in the first region obtained in the foregoing steps may also be displayed on the display 300. In one embodiment, the elasticity parameters or the propagation path of the shear wave may be displayed on the display 300 simultaneously with the conventional ultrasound image of the body tissue under examination obtained in step S001.

In these embodiments, the conventional imaging process for obtaining the conventional ultrasound images and the transient elastography process for obtaining the elasticity parameters can be achieved by the same probe, that is, with one same probe, both the conventional ultrasound images and the elasticity parameters of the tissue can be obtained. Therefore, the doctor can observe the images of the internal of the body tissue under examination when performing the elasticity measurement, which can facilitate the doctor to find the tissue on which the elasticity measurement is desired to be performed.

Figure 6:
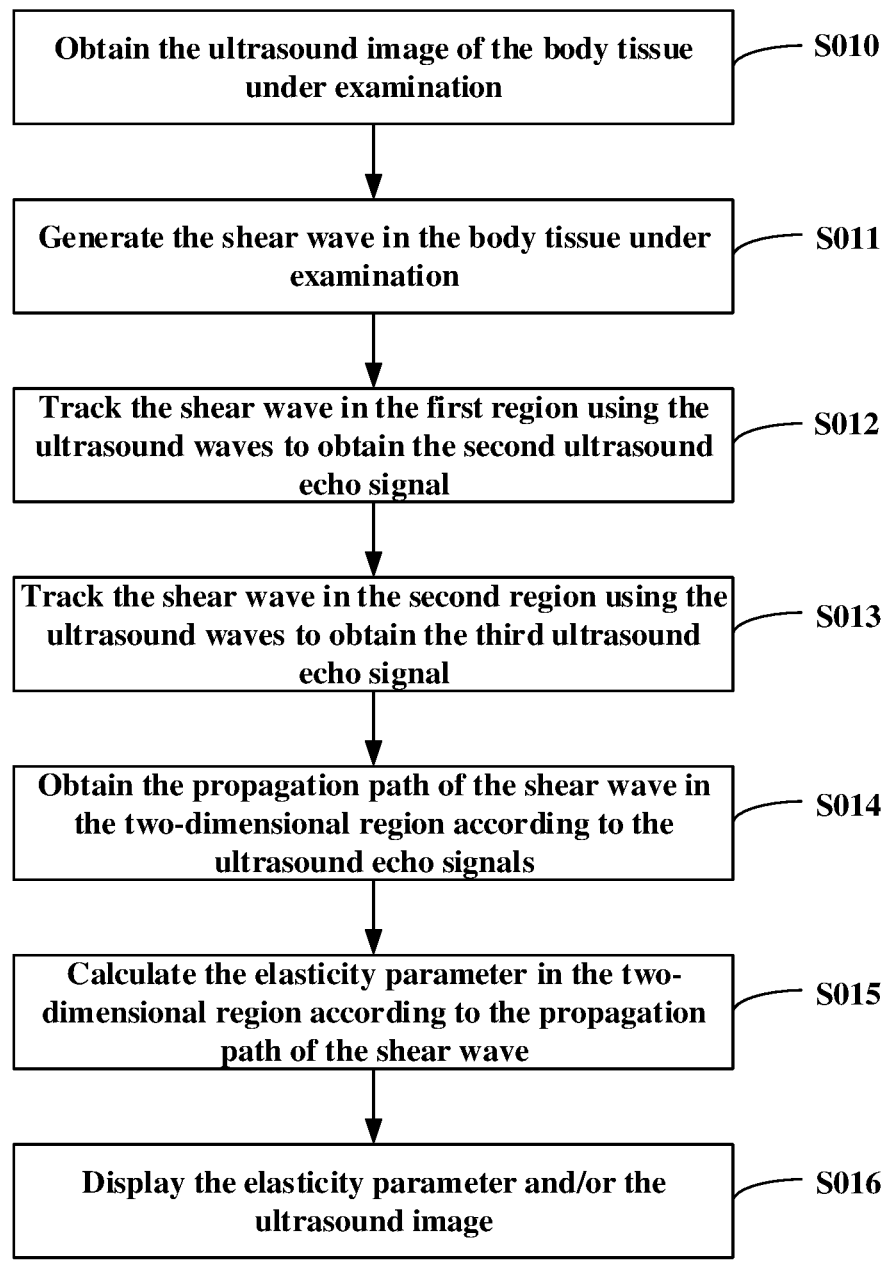
FIG. 6 is a schematic flowchart of an ultrasound elastography method in one embodiment.
Figure 7:
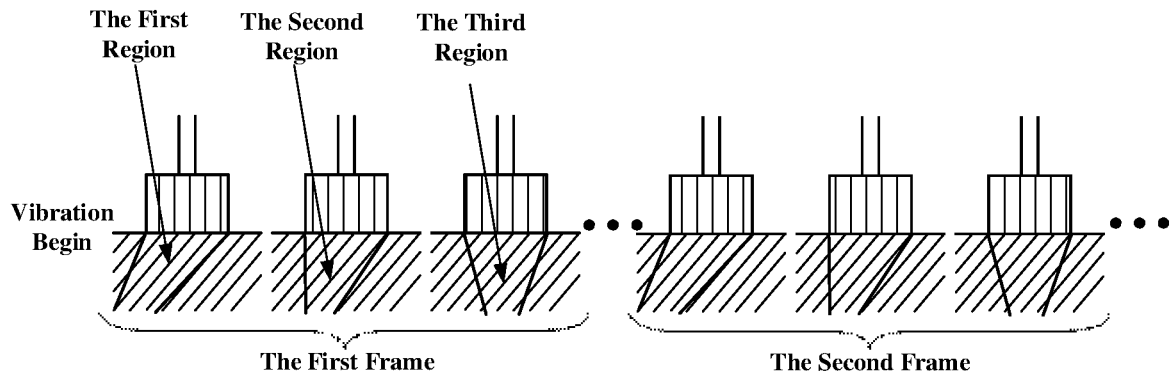
FIG. 7 schematically shows the scanning process in one embodiment.

Referring to FIG. 6 and FIG. 7, in one embodiment of the present disclosure, an ultrasound elastography method implemented using the foregoing ultrasound elastography system may include the following steps.

In step S010, the ultrasound image of the body tissue under examination may be obtained. This step may be the same as or similar to step S001 above and will not be described in detail here.

In step S011, the shear wave may be generated in the body tissue under examination. This step may be the same as or similar to step S002 above, and will not be described in detail here.

In step S012, the ultrasound waves may be used to track the shear wave in the first region to obtain the second ultrasound echo signals.

In this step, similar to step S003 above, After the shear wave is generated in step S011, the control and data processor 200 may send excitation pulses to the ultrasound transducer 150 to excite at least part of the array elements in the ultrasound transducer 150 to transmit the ultrasound waves to the body tissue under examination. Each time the ultrasound waves are transmitted, all or a part of the array elements in the ultrasound transducer 150 may participate in the transmitting. By controlling the time when the array elements participating in the transmitting (i.e., the array elements to be excited in this transmitting) are excited by the excitation pulses, the direction and/or width of the ultrasound beam finally formed by the ultrasound waves transmitted by these array elements participating in this transmitting can be adjusted, such that the ultrasound waves transmitted by the array elements participating in the transmitting form an ultrasound beam that propagates along a desired angle or in a desired region (in other words, covers the desired region). In this embodiment, the control and data processor 200 may control the time when the array elements to be excited (i.e., the array elements participating in the current transmitting) are excited by the excitation pulses, such that the ultrasound waves transmitted thereby form an ultrasound beam covering the first region of the body tissue under examination in which the generated shear wave at least partly propagates. Therefore, this ultrasound beam can track the propagation process of the shear wave in this first region.

In this embodiment, the ultrasound beam formed by the ultrasound waves transmitted by the at least part of the array elements may be a focused ultrasound beam or an unfocused ultrasound beam, such as a plan ultrasound beam or a diverged ultrasound beam.

The ultrasound transducer 150 may receive the ultrasound echoes from the first region to obtain the ultrasound echo signals. Here, the ultrasound echo signals obtained from the ultrasound echoes from the first region in the present embodiment will still be referred to as the second ultrasound echo signals.

The process of transmitting the ultrasound beam covering the first region and receiving the ultrasound echoes to obtain the second ultrasound echo signals may be repeated multiple times.

Similarly, in step S013, the control and data processor 200 may control or adjust the time when the array elements to be excited (i.e., the array elements participating in the current transmitting) are excited by the excitation pulses to change the direction of the ultrasound beam formed by the ultrasound waves transmitted by the excited array elements, such that the ultrasound waves transmitted by the excited array elements form an ultrasound beam covering the second region in the body tissue under examination in which the generated shear wave at least partially propagate. Therefore, this ultrasound beam can track the propagation process of the shear wave in the second region.

In this embodiment, the ultrasound beam formed by the ultrasound waves transmitted by the at least part of the array elements may be a focused ultrasound beam or an unfocused ultrasound beam, such as a plan ultrasound beam or a diverged ultrasound beam.

The ultrasound transducer 150 may receive the ultrasound echoes from the second region to obtain the ultrasound echo signals. Herein, the ultrasound echo signals obtained from the ultrasound echoes from the second region will be referred to as the third ultrasound echo signals.

The process of transmitting the ultrasound beam covering the second region and receiving the ultrasound echoes to obtain the third ultrasound echo signals may be repeated multiple times.

In this embodiment, it may also be possible to similarly transmit ultrasound beams covering the third region or more regions and receive ultrasound echoes from the regions to obtain corresponding ultrasound echo signals, as shown in FIG. 7.

In step S014, the shear wave propagation path in the two-dimensional region may be obtained according to the ultrasound echo signals.

The first region and the second region may be adjacent or partially overlapped, so as to form a two-dimensional region. In the case that the ultrasound beams covering corresponding regions are transmitted to more regions, these regions may adjacent to or partially overlapped with each other, and all these regions may form a two-dimensional region. In step S014, the control and data processor 200 may obtain the propagation path of the shear wave in this two-dimensional region (that is, the two-dimensional region including the first region and the second region, or the two-dimensional region including more regions) according to the second ultrasound echo signals and the third ultrasound echo signals or the ultrasound echo signals from the more regions. For example, in one embodiment, the control and data processor 200 may perform correlation calculation on the ultrasound echo signals obtained at different times covering the same region, so as to obtain the propagation path of the shear wave in this region. Similar correlation calculation may be performed on all regions forming the two-dimensional region to obtain the propagation paths of the shear wave in all regions forming the two-dimensional region, thereby obtaining the propagation path of the shear wave in this two-dimensional region.

In step S015: the elasticity parameters in the two-dimensional region may be calculated according to the shear wave propagation path.

In this step, similar to step S004 above, a similar method may be used to calculate the elasticity parameters in the two-dimensional region according to the shear wave propagation path. The elasticity parameter may be the propagation speed of the shear wave in the two-dimensional region, the Young's modulus of the body tissue under examination in the two-dimensional region, the shear modulus of the body tissue under examination in the two-dimensional region, the attenuation of the shear wave in the body tissue under examination in the two-dimensional region or the ratio of the elasticity parameters of the body tissue under examination at different positions in the two-dimensional region, etc.

In one embodiment, these elasticity parameters may be directly calculated in the two-dimensional region according to the shear wave propagation path in the two-dimensional region.

In another embodiment, the elasticity parameters in each region may be calculated according to the shear wave propagation path in each region, respectively, and the elasticity parameters in the two-dimensional region may be obtained by combining the elasticity parameters in these regions. For example, in one embodiment, the elasticity parameter in the first region may be obtained according to the shear wave propagation path in the first region, such as the propagation speed of the shear wave in the first region, the Young's modulus of the body tissue under examination in the first region, the shear modulus of the body tissue under examination in the first region, the attenuation of the shear wave in the body tissue under examination in the first region or the ratio of the elasticity parameters of the body tissue under examination at different positions in the first region, etc., and the elasticity parameter in the second region may be obtained according to the shear wave propagation path in the second region, such as the propagation speed of the shear wave in the second region, the Young's modulus of the body tissue under examination in the second region, the shear modulus of the body tissue under examination in the second region, the attenuation of the shear wave in the body tissue under examination in the second region or the ratio of the elasticity parameters of the body tissue under examination at different positions in the second region, etc. According to the elasticity parameter in the first region and the elasticity parameter in the second region, the elasticity parameter of the two-dimensional region formed by the first region and the second region may be obtained.

In step S016, the elasticity parameter and/or the ultrasound image may be displayed.

The elasticity parameters in the two-dimensional region obtained in step S015 may be displayed on the display 300. The elasticity parameters of this two-dimensional region may be displayed as a two-dimensional image frame, which may be in various forms, such as a numerical image frame, a pseudo-color image frame using color coding, a gray image frame, or the like. Generally, when the elasticity parameters in the multiple regions (for example, the first region and the second region) forming the two-dimensional region are all calculated once, these elasticity parameters may be combined to form one frame of two-dimensional elasticity image. When the scanning is continued to obtain the elasticity parameters in these regions, more frames of two-dimensional elasticity images may be obtained.

In these embodiments, not only both the conventional imaging process for obtaining the conventional ultrasound images and the transient elastography process for obtaining the elasticity parameters can be achieved through one same probe, but also two-dimensional transient elasticity images in the two-dimensional region can be obtained so as to provide the doctors with two-dimensional distribution of the transient elasticity parameters in the two-dimensional region, thereby facilitating the doctors to diagnose the body tissue under examination.

In one embodiment, the shear wave may be generated for multiple times. After the shear wave is generated once, the ultrasound echo signals from a part of the multiple regions or the propagation path of the shear wave in the corresponding region or the elasticity parameter in the corresponding region may be obtained using the methods above; after the shear wave is generated again, the ultrasound echo signals from another part of the multiple regions or the propagation path of the shear wave in the corresponding region or the elasticity parameter in the corresponding region may be obtained. After multiple generations of the shear waves, for all of the multiple regions, the ultrasound echo signals therefrom or the propagation path of the shear waves therein or the elasticity parameter therein may be obtained.

For example, in one embodiment, the ultrasound elastography method may include:
  generating the shear wave in the body tissue under examinations;
  exciting at least part of the array elements of the ultrasound transducer to transmit the ultrasound waves and control the excitation time of each array element to be excited such that the ultrasound waves transmitted by the excited array elements form the ultrasound beam covering the first region in the body tissue under examination, where the shear wave at least partially propagates in the first region;
  receiving the ultrasound echoes from the first region to obtain the second ultrasound echo signals;
  generating the shear waves in the body tissue under examination again;
  exciting at least part of the array elements of the ultrasound transducer to transmit the ultrasound waves and control the excitation time of each array element to be excited such that the ultrasound waves transmitted by the excited array elements form the ultrasound beam covering the second region in the body tissue under examination, where the shear wave at least partially propagates in the second region;
  receiving the ultrasound echoes from the second region to obtain the third ultrasound echo signal; and
  obtaining the propagation path of the shear wave in the two-dimensional region including the first region and the second region at least according to the second ultrasound echo signals and the third ultrasound echo signals.

In this embodiment, the shear waves generated twice or more times may be the same shear waves generated at the same position with the same parameters.

Figure 8:
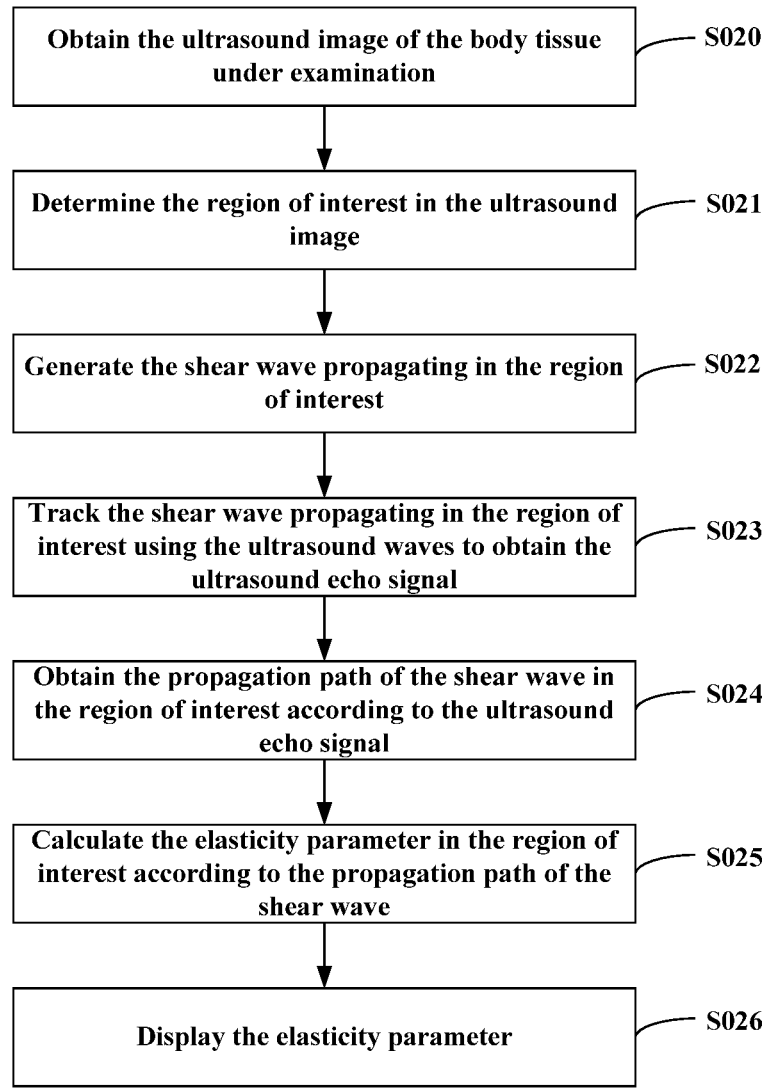
FIG. 8 is a schematic flowchart of an ultrasound elastography method in one embodiment.

In one embodiment, during the ultrasound elastography, the conventional ultrasound image of the body tissue under examination may be obtained first. Thereafter, a region of interest may be determined based on the ultrasound image, and the elasticity of the body tissue in the region of interest may be measured, as shown in FIG. 8. The user or the ultrasound elastography system can determine the region in which the elasticity is desired to be measured through the conventional ultrasound image. The ultrasound elastography system can more accurately generate and track the shear wave passing through the region of interest to obtain the elasticity parameters in the region of interest. In this way, the target whose elasticity is desired to be measured can be located more accurately, so that the doctor can quickly and accurately obtain the elasticity parameters of the region of interest. Therefore, it is easier to use.

Referring to FIG. 8, in this embodiment, in step S020, the control and data processor 200 may excite the ultrasound probe 100 to transmit the ultrasound waves to the body tissue under examination and receive the ultrasound echoes to obtain the first ultrasound echo signals, obtain the ultrasound image of the body tissue under examination according to the first ultrasound echo signals, and display the ultrasound image on the display 300. The ultrasound image may be a B-mode image, a C-mode image, a D-mode image, or other mode image. This step S020 may be similar to step S001 above, and will not be described in detail here.

In step S021, the control and data processor 200 may determine the region of interest on the ultrasound image. The control and data processor 200 may determine the region of interest according to a signal input by the user through a human-computer interaction device (not shown in FIG. 1) for selecting or defining the region of interest. For example, the user can select or draw the range of the region of interest on the ultrasound image displayed on the display 300 through the human-computer interaction device, such as drawing a frame for defining the region of interest, etc., and the control and data processor 200 may receive the input of the user and determine the region of interest on the ultrasound image according to the input.

In one embodiment, the control and data processor 200 may also automatically determine the region of interest. For example, the control and data processor 200 may process the ultrasound image according to preset rules to identify the region of interest.

After the region of interest is determined, in step S022, the shear wave propagating in the region of interest may be generated. For example, the control and data processor 200 may control the vibrator 110 provided in the ultrasound probe 100 to drive the ultrasound transducer 150 to vibrate to generate the shear wave propagating in the region of interest, or control a separate vibrator that is provided separately from the ultrasound probe 100 to vibrate to generate the shear wave propagating in the region of interest. In this process, based on the position of the region of interest determined on the ultrasound image, the contact position of the ultrasound transducer 150 of the ultrasound probe 100 with the surface of the body tissue under examination or the contact position of the separate vibrator provided separately from the ultrasound probe 100 with the body tissue under examination may be adjusted, such that the generated shear wave can be able to or can better propagate in the region of interest, thereby improving the accuracy and reliability of elasticity measurement.

In step S023, the control and data processor 200 may excite at least part of the array elements of the ultrasound transducer 150 to transmit ultrasound waves and control the excitation time of each array element to be excited such that the ultrasound waves transmitted by the excited array elements form the ultrasound beam covering the region of interest, and receive the ultrasound echoes from the region of interest through the ultrasound probe to obtain the ultrasound echo signals. Here, the ultrasound beam formed by the ultrasound waves transmitted by the excited array elements may be a focused ultrasound beam or an unfocused ultrasound beam.

In step S024, the control and data processor 200 may obtain the propagation path of the shear wave in the region of interest according to the ultrasound echo signals obtained in step S023. The method for obtaining the propagation path in this step may be similar to the methods in step S003 or S014 above, and will not be described in detail here.

In one embodiment, the shear wave in the region of interest may be tracked by regions, and the shear wave propagation path in the entire region of interest may be obtained according to the ultrasound echo signals obtained from these regions or according to the shear wave propagation paths in these regions respectively obtained.

For example, in one embodiment, in steps S023 and S024, the control and data processor 200 may excite at least part of the array elements of the ultrasound transducer to transmit the ultrasound waves and control the excitation time of each array element to be excited such that the ultrasound waves transmitted by the excited array elements form the ultrasound beam covering the first region in the region of interest, and receive the ultrasound echoes from the first region through the ultrasound probe to obtain the second ultrasound echo signals. Subsequently, the control and data processor 200 may adjust the excitation time of the array elements to be excited to change the direction of the ultrasound beam formed by the ultrasound waves transmitted by the excited array elements such that the ultrasound beam formed by the ultrasound waves transmitted by the excited array elements covers the second region in the region of interest, and receive the ultrasound echoes from the second region to obtain the third ultrasound echo signals. Similarly, the control and data processor 200 may also control or adjust the excitation time of the array elements to be excited to change the direction of the ultrasound beam formed by the ultrasound waves transmitted thereby to scan more regions with the ultrasound beam to track the shear wave propagating therein. All of these regions form the region of interest. Correspondingly, the control and data processor 200 may obtain the propagation path of the shear wave in the region of interest at least according to the second ultrasound echo signals and the third ultrasound echo signals.

In step S025, the control and data processor 200 may calculate the elasticity parameter representing the elasticity of the body tissue in the region of interest according to the propagation path of the shear wave in the region of interest. The elasticity parameter may include the propagation speed of the shear wave in the region of interest, the Young's modulus of the body tissue under examination in the region of interest, the shear modulus of the body tissue under examination in the region of interest, the attenuation of the shear wave in the body tissue under examination in the region of interest, the ratio of elasticity parameters of the body tissue under examination at different positions in the region of interest, or other elasticity parameters representing the elasticity of the tissue.

In this step, the method for calculating the elasticity parameter may be similar to the methods in step S004 or S015 above, and will not be described in detail here.

In one embodiment, the control and data processor 200 may obtain the elasticity image of the entire region of interest, such as a two-dimensional elasticity image or a three-dimensional elasticity image, according to the obtained elasticity parameter. In this embodiment, the elasticity image may be in various forms, such as a numerical image, a pseudo-color image using color coding, a grayscale image, or the like.

In step S026, the control and data processor 200 may display the obtained elasticity parameter on the display 300. In this embodiment, the elasticity parameter may be displayed as a numerical value or a graph, etc., or may be displayed as the elasticity image as described above.

The embodiments above may be implemented entirely or partly by software, hardware, firmware or any combination thereof. When implemented by software, they can be implemented entirely or partly in the form of a computer program product.

The computer program product may include one or more computer instructions. When the computer instructions are loaded and executed in the computer, the processes or functions described in the embodiments of the present disclosure may be generated in whole or in part. The computer may be a general-purpose computer, a special-purpose computer, a computer network, or other programmable devices. The computer instructions may be stored in a computer-readable storage medium, or be transmitted from one computer-readable storage medium to another computer-readable storage medium. For example, the computer instructions may be transmitted from a website, computer, server or data center to another website, computer, server or data center via wired (such as coaxial cable, optical fiber, Digital Subscriber Line (DSL)) or wireless (such as infrared, wireless, microwave, etc.) connection. The computer-readable storage medium may be any available medium that can be used for storing by a computer or a data storage device such as an integrated server or data center which include one or more available media. The available medium may be a magnetic medium (such as a floppy disk, a hard disk, a magnetic tape), an optical medium (such as a DVD), a semiconductor medium (such as a solid state hard disk (SSD) or the like.

Those skilled in the art can clearly understand that, regarding the specific working process of the system, device and unit described above, reference may be made to the corresponding processes in the methods described above, which, for the convenience and conciseness of the description, will not be repeated here.

It should be understood that in the embodiments of the present disclosure the disclosed systems, devices and methods may be implemented in other ways. For example, the devices described above are only illustrative. For example, the division of the units is only a logical function division, and there may be other divisions in actual implementation. For example, multiple units or components may be combined or be integrated into another system. Some features may be ignored or not implemented. In addition, the displayed or discussed mutual coupling or direct coupling or communication connection may be indirect coupling or communication connection through some interfaces, devices or units, and may be in electrical, mechanical or other forms.

The units described as separate components may or may not be physically separated. The components displayed as units may or may not be physical units, that is, they may be located in one place, or they may be distributed on multiple network units. Some or all of the units may be selected according to actual needs to achieve the objectives of the solutions of the embodiments.

In addition, the functional units in the embodiments of the present disclosure may be integrated into one unit. Alternatively, the units may exist alone physically. Alternatively, two or more units may be integrated into one unit. The integrated unit may be implemented in the form of hardware or software functional unit.

In the case that the integrated unit is implemented in the form of a software functional unit and sold or used as an independent product, it may be stored in a computer readable storage medium. Based on this understanding, the essential part or the part that contributes to the existing technology or all or part of the technical solutions of the present disclosure may be embodied in the form of a software product. The software product may be stored in a storage medium, and may include multiple instructions which may be used to make a computer device (which may be a personal computer, a server, or a network device, etc.) to execute all or part of the steps of the method described in the embodiments of the present disclosure. The storage media may include a U disk, a mobile hard disk, a read-only memory (ROM), a random access memory (RAM), a magnetic disk, an optical disk or other media that can store program code.

The technical features in the embodiments above may be combined arbitrarily. In order to make the description concise, all possible combinations of the technical features in the embodiments above are not described. However, as long as there is no contradiction in the combinations of these technical features, these combinations should all be in the scope of the present disclosure.

The embodiments above only show several implementations of the present disclosure, and the descriptions thereof are relatively specific and detailed. However, they should not be understood as limitation to the scope of the present disclosure. It should be noted that for those of ordinary skill in the art, without departing from the concept of the present disclosure, several modifications and improvements may be made, which shall all fall within the protection scope of the present disclosure. Therefore, the protection scope of the present disclosure should be determined by the appended claims.

The invention claimed is:

1. An ultrasound elastography method, comprising:
    exciting an ultrasound probe to transmit ultrasound waves to a body tissue under examination and receive ultrasound echoes to obtain a first ultrasound echo signal, wherein the ultrasound probe comprises an ultrasound transducer provided with multiple array elements;
    obtaining an ultrasound image of the body tissue under examination according to the first ultrasound echo signal;
    generating a shear wave in the body tissue under examination;
    exciting a portion of the array elements of the ultrasound transducer to transmit ultrasound waves and control an excitation time of the portion of the array elements such that the ultrasound waves transmitted by the portion of the array elements form a first unfocused ultrasound beam covering a first region in the body tissue under examination, wherein the shear wave propagates at least partially in the first region, and the first unfocused ultrasound beam tracks a propagation process of the shear wave in the first region;
    receiving ultrasound echoes from the first region to obtain second ultrasound echo signals;
    performing correlation calculation on the second ultrasound echo signals obtained at different times to obtain a first propagation path of the shear wave in the first region;
    exciting the portion of the array elements of the ultrasound transducer to transmit ultrasound waves and control an excitation time of the portion of the array elements such that the ultrasound waves transmitted by the portion of the array elements form a second unfocused ultrasound beam covering a second region in the body tissue under examination, wherein the shear wave propagates at least partially in the second region, and the second unfocused ultrasound beam tracks a propagation process of the shear wave in the second region, wherein the first region in the body tissue under examination has a first area and the second region in the body tissue under examination has a second area, wherein the second region is different from the first region and at least partially overlaps with the first region, and the first region and the second region form a two-dimensional region;
    receiving ultrasound echoes from the second region to obtain third ultrasound echo signals;
    performing correlation calculation on the third ultrasound echo signals obtained at different times to obtain a second propagation path of the shear wave in the second region; and
    simultaneously displaying, by a display device, the ultrasound image, the first propagation path, and the second propagation path.

2. The method of claim 1, further comprising: calculating a first elasticity parameter in the first region based on the first propagation path of the shear wave in the first region, calculating a second elasticity parameter in the second region based on the second propagation path of the shear wave in the second region, and combining the first elasticity parameter in the first region and the second elasticity parameter in the second region to obtain an elasticity parameter representing an elasticity of the body tissue under examination in the two-dimensional region.

3. The method of claim 2, further comprising: displaying the elasticity parameter.

4. The method of claim 2, wherein the elasticity parameter comprises a propagation speed of the shear wave in the two-dimensional region, a Young's modulus of the body tissue under examination in the two-dimensional region, a shear modulus of the body tissue under examination in the two-dimensional region, an attenuation of the shear wave in the body tissue under examination in the two-dimensional region, or a ratio of elasticity parameters of the body tissue under examination at different positions in the two-dimensional region.

5. The method of claim 2, further comprising: displaying, by the display device, the elasticity parameter representing the elasticity of the body tissue under examination in the two-dimensional region.

6. The method of claim 2, further comprising: displaying, by the display device, the elasticity parameter representing the elasticity of the body tissue under examination in the two-dimensional region as a two-dimensional image.

7. An ultrasound elastography method, comprising:
    generating a shear wave in a body tissue under examination;
    exciting a portion of array elements of an ultrasound transducer to transmit ultrasound waves and control an excitation time of the portion of the array elements such that the ultrasound waves transmitted by the portion of the array elements form a first unfocused ultrasound beam covering a first region in the body tissue under examination, wherein the shear wave propagates at least partially in the first region, and the first unfocused ultrasound beam tracks a propagation process of the shear wave in the first region;

receiving ultrasound echoes from the first region to obtain first ultrasound echo signals;

performing correlation calculation on the first ultrasound echo signals obtained at different times to obtain a first propagation path of the shear wave in the first region;

adjusting the excitation time of the portion of the array elements in the ultrasound transducer to change a direction of the first unfocused ultrasound beam formed by the ultrasound waves transmitted by the portion of the array elements such that a second unfocused ultrasound beam formed by the ultrasound waves transmitted by the portion of the array elements covers a second region in the body tissue under examination, wherein the shear wave propagates at least partially in the second region, and the second unfocused ultrasound beam tracks a propagation process of the shear wave in the second region, wherein the first region in the body tissue under examination has a first area and the second region in the body tissue under examination has a second area, wherein the second region is different from the first region and at least partially overlaps with the first region, and the first region and the second region form a two-dimensional region;

receiving ultrasound echoes from the second region to obtain second ultrasound echo signals;

performing correlation calculation on the second ultrasound echo signals obtained at different times to obtain a second propagation path of the shear wave in the second region; and simultaneously displaying, by a display device, an ultrasound image of the body tissue under examination, the first propagation path, and the second propagation path.

8. The method of claim 7, further comprising:

calculating a first elasticity parameter in the first region based on the first propagation path of the shear wave in the first region, calculating a second elasticity parameter in the second region based on the second propagation path of the shear wave in the second region, and combining the first elasticity parameter in the first region and the second elasticity parameter in the second region to obtain an elasticity parameter representing an elasticity of the body tissue under examination in the two-dimensional region.

9. The method of claim 8, further comprising: displaying, by the display device, the elasticity parameter representing the elasticity of the body tissue under examination in the two-dimensional region.

10. The method of claim 8, further comprising: displaying, by the display device, the elasticity parameter representing the elasticity of the body tissue under examination in the two-dimensional region as a two-dimensional image.

11. The method of claim 8, wherein the elasticity parameter comprises a propagation speed of the shear wave in the two-dimensional region, a Young's modulus of the body tissue under examination in the two-dimensional region, a shear modulus of the body tissue under examination in the two-dimensional region, an attenuation of the shear wave in the body tissue under examination in the two-dimensional region, or a ratio of elasticity parameters of the body tissue under examination at different positions in the two-dimensional region.

12. An ultrasound elastography method, comprising:

exciting an ultrasound probe to transmit ultrasound waves to a body tissue under examination and receive ultrasound echoes to obtain a first ultrasound echo signal, wherein the ultrasound probe comprises an ultrasound transducer provided with multiple array elements;

obtaining an ultrasound image of the body tissue under examination according to the first ultrasound echo signal;

determining a region of interest in the ultrasound image;

based on the determined region of interest, generating a shear wave in the body tissue under examination such that the generated shear wave at least partially propagates in the region of interest;

exciting a portion of the array elements of the ultrasound transducer to transmit ultrasound waves and controlling an excitation time of the portion of the array elements such that the ultrasound waves transmitted by the portion of the array elements form a first unfocused ultrasound beam covering a first region of the region of interest, wherein the first unfocused ultrasound beam tracks a propagation process of the shear wave in the first region of the region of interest;

receiving ultrasound echoes from the first region of the region of interest to obtain second ultrasound echo signals;

performing correlation calculation on the second ultrasound echo signals obtained at different times to obtain a first propagation path of the shear wave in the first region of the region of interest;

exciting the portion of the array elements of the ultrasound transducer to transmit ultrasound waves and controlling an excitation time of the portion of the array elements such that the ultrasound waves transmitted by the portion of the array elements form a second unfocused ultrasound beam covering a second region of the region of interest, wherein the second unfocused ultrasound beam tracks a propagation process of the shear wave in the second region of the region of interest, wherein the first region of the region of interest has a first area and the second region of the region of interest has a second area, wherein the second region is different from the first region and at least partially overlaps with the first region, and the first region and the second region form the region of interest;

receiving ultrasound echoes from the second region of the region of interest to obtain third ultrasound echo signals;

performing correlation calculation on the third ultrasound echo signals obtained at different times to obtain a second propagation path of the shear wave in the second region of the region of interest; and simultaneously displaying, by a display device, the ultrasound image, the first propagation path, and the second propagation path.

13. The method of claim 12, further comprising: calculating a first elasticity parameter in the first region of the region of interest based on the first propagation path of the shear wave in the first region of the region of interest, calculating a second elasticity parameter in the second region of the region of interest based on the second propagation path of the shear wave in the second region of the region of interest, and combining the first elasticity parameter in the first region and the second elasticity parameter in the second region to obtain an elasticity parameter representing an elasticity of the body tissue under examination in the region of interest.

14. The method of claim 13, further comprising:
obtaining an elasticity image in the region of interest according to the elasticity parameter; and
displaying, by the display device, the elasticity image.

15. The method of claim 13, wherein the elasticity parameter comprises a propagation speed of the shear wave in the region of interest, a Young's modulus of the body tissue under examination in the region of interest, a shear modulus of the body tissue under examination in the region of interest, an attenuation of the shear wave in the body tissue under examination in the region of interest or a ratio of elasticity parameters of the body tissue under examination at different positions in the region of interest.

* * * * *